(12) United States Patent
Butler et al.

(10) Patent No.: US 8,475,461 B2
(45) Date of Patent: Jul. 2, 2013

(54) INSTRUMENTS FOR INSTALLING MULTI-SECTION INTERVERTEBRAL SPINAL IMPLANTS

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 445 days.

(21) Appl. No.: 12/797,360

(22) Filed: Jun. 9, 2010

(65) Prior Publication Data

US 2010/0318092 A1 Dec. 16, 2010

Related U.S. Application Data

(60) Provisional application No. 61/185,810, filed on Jun. 10, 2009.

(51) Int. Cl.
*A61B 17/88* (2006.01)
*A61B 17/70* (2006.01)

(52) U.S. Cl.
USPC ............................. 606/86 A; 606/914

(58) Field of Classification Search
USPC ................ 606/86 A, 99, 246, 279, 914
See application file for complete search history.

(56) References Cited

U.S. PATENT DOCUMENTS

| | | | |
|---|---|---|---|
| 5,207,692 A | 5/1993 | Kraus et al. | |
| 6,551,333 B2 * | 4/2003 | Kuhns et al. | 606/151 |
| 6,595,998 B2 * | 7/2003 | Johnson et al. | 606/90 |
| 7,252,686 B2 * | 8/2007 | Carrison et al. | 623/17.16 |
| 8,034,109 B2 * | 10/2011 | Zwirkoski | 623/17.11 |
| 2002/0183761 A1 | 12/2002 | Johnson et al. | |
| 2005/0187559 A1 * | 8/2005 | Raymond et al. | 606/90 |
| 2008/0221588 A1 | 9/2008 | Hollis et al. | |

OTHER PUBLICATIONS

International Preliminary Report on Patentability for International application No. PCT/US10/38099, dated May 23, 2011, 8 pages.

\* cited by examiner

*Primary Examiner* — Nicholas Woodall
*Assistant Examiner* — Larry E Waggle, Jr.
(74) *Attorney, Agent, or Firm* — Foley & Lardner LLP

(57) ABSTRACT

Instruments are provided for delivering and installing a multi-section spinal implant in-situ one section at a time by sequential deployment and assembling of the multi-section spinal implant sections into an intervertebral space. An advancement mechanism provides controlled deployment of individual implant sections from the instrument. Each instrument accepts a plurality of implant sections that are stacked on a deployment rod. Activation of the advancement mechanism advances a pusher against a rearward implant section of the implant section stack. This, in turn, advances all or some of the implant sections such that the forward most implant section exits the instrument. As the advancement mechanism is further activated, additional implant sections are deployed from the instrument. In this manner, a multi-section spinal implant of any number of implant sections may be delivered and assembled in situ. In one form, the advancement mechanism comprises an indexing mechanism. In another form, the advancement mechanism comprises a ratchet device provided on and between a trigger and an advancement tube.

16 Claims, 11 Drawing Sheets

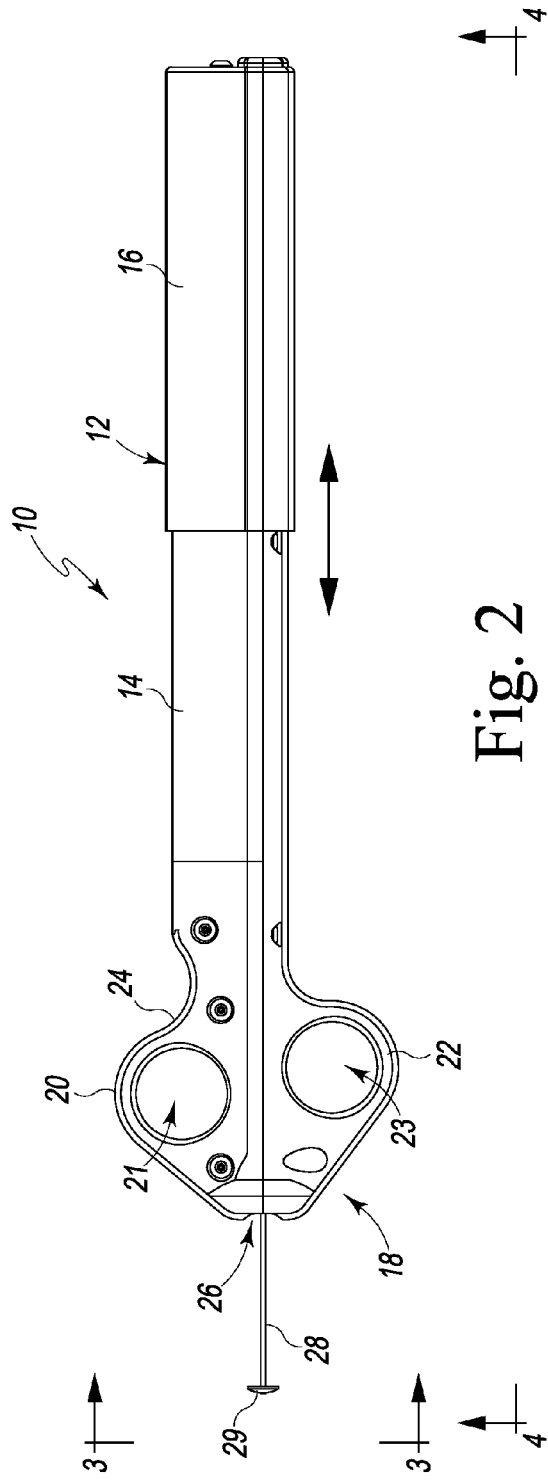
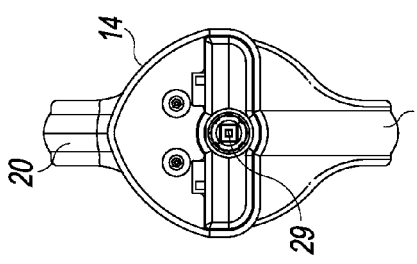
Fig. 2
Fig. 3

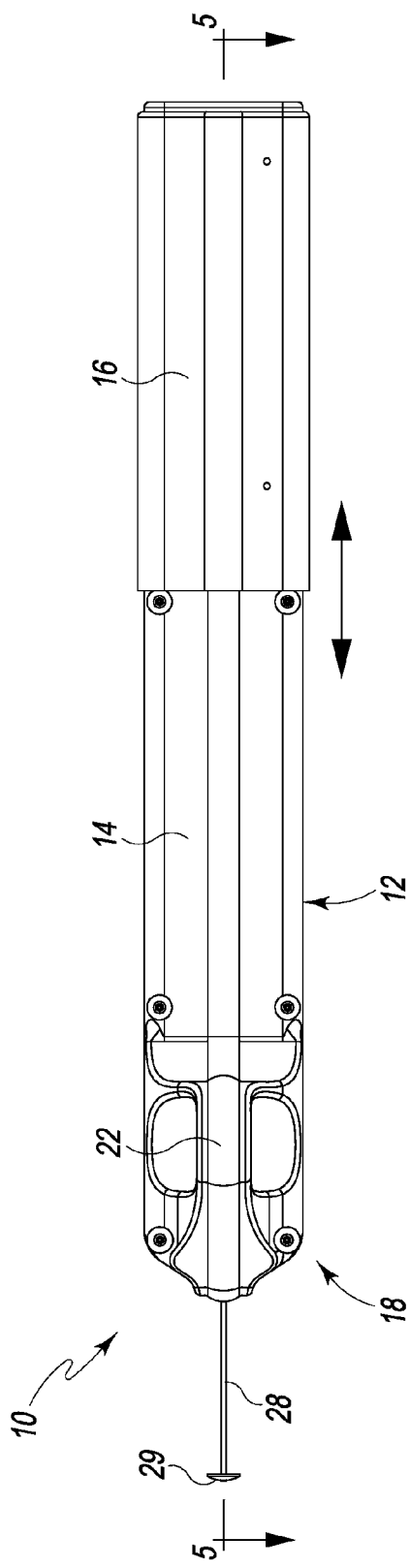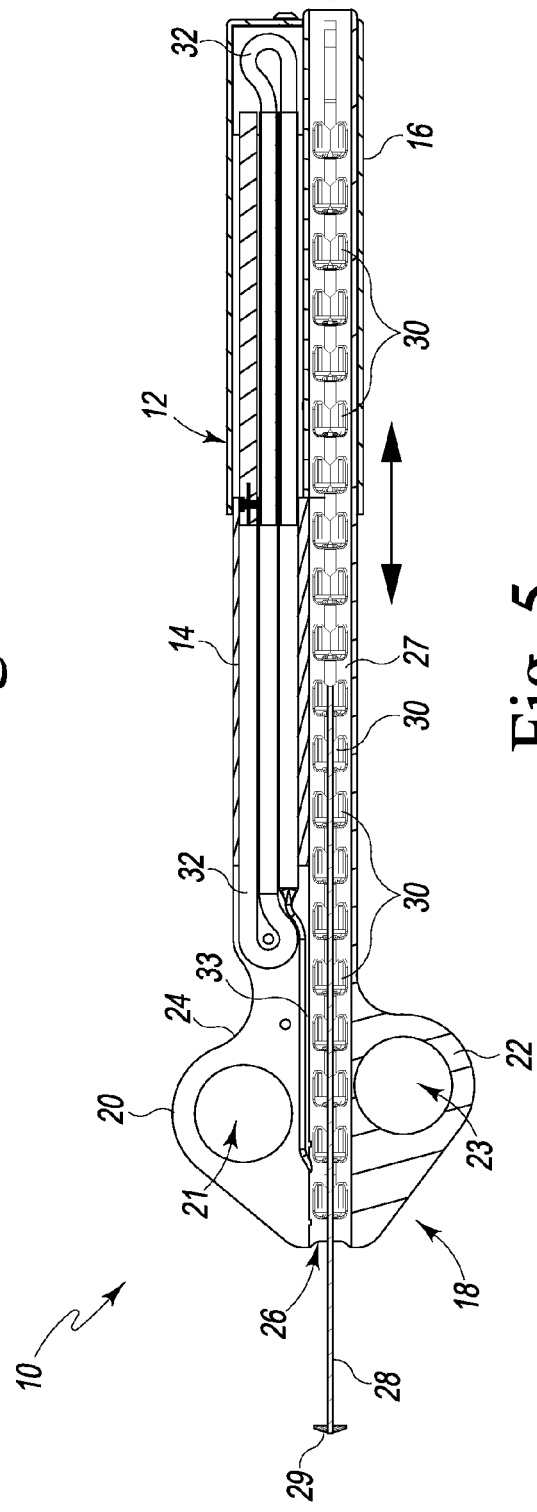

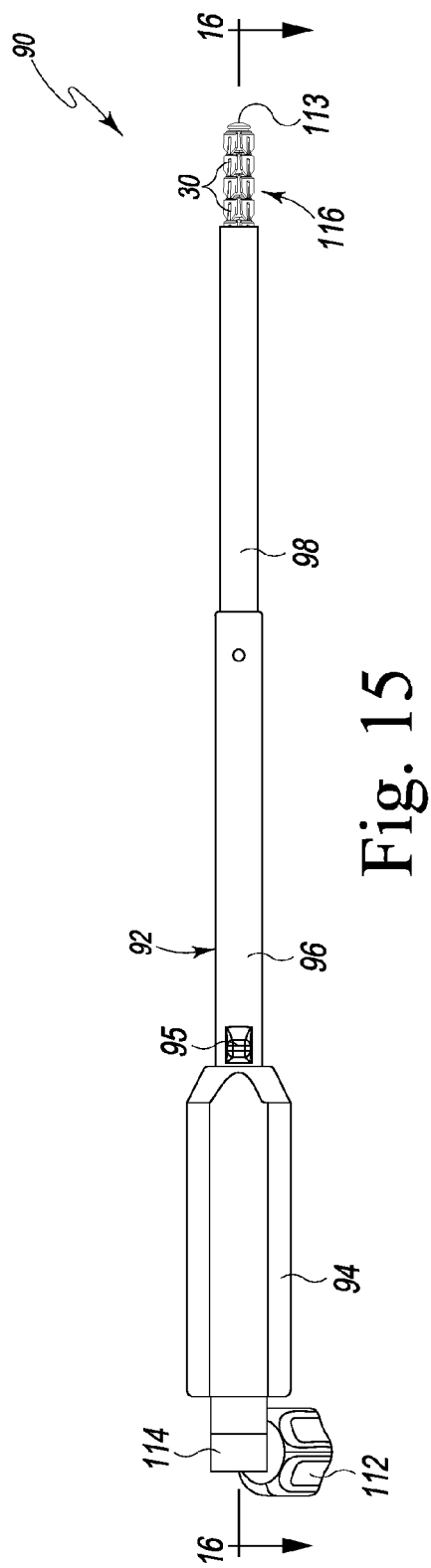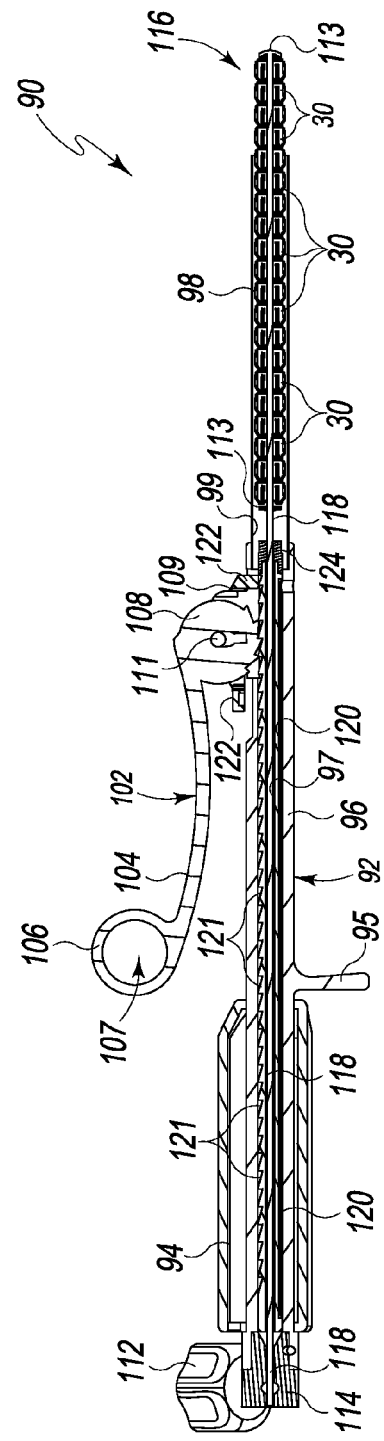

INSTRUMENTS FOR INSTALLING MULTI-SECTION INTERVERTEBRAL SPINAL IMPLANTS

RELATED APPLICATIONS

This patent application claims the benefit of and/or priority under 35 U.S.C. §119(e) to U.S. Provisional Patent Application Ser. No. 61/185,810 filed Jun. 10, 2009, entitled "Instruments For Installing Multi-Section Intervertebral Spinal Implant" the entire contents of which is specifically incorporated herein by this reference.

BACKGROUND OF THE INVENTION

1. Field of the Invention

The present invention relates to devices for installing spinal implants during spinal surgery and, more particularly, to devices for installing multi-section intervertebral spinal implants.

2. Background Information

There are many medical situations such as disease, injury, deformity or the like where it is necessary to provide support and/or alignment to and between adjacent vertebrae of a patient's spine. It may also be necessary in these instances and others to hold and/or fix a desired relationship between adjacent vertebrae and/or provide a foundation between adjacent vertebrae for fusion of the vertebrae. In order to accomplish this goal, spinal surgery is performed that places one or more spinal implants between adjacent vertebrae. The spinal implants are known as intervertebral spinal implants.

During the spinal surgery, one or more intervertebral spinal implants are inserted into the space between adjacent vertebrae (the intervertebral space) where a spinal disc normally exists but which has been removed. An instrument is used to insert the intervertebral spinal implant. When the intervertebral spinal implant has a uni-body construction (i.e. consists of a single component) the delivery and/or installation instrument may consist of a cannula or other simple device. However, when the intervertebral spinal implant has a multi-body construction (i.e. consists of multiple components) the delivery and/or installation instrument can become more complicated than a simple cannula. Moreover, the delivery/installation instrument design may be dependant on the configuration of the multi-body intervertebral spinal implant or the manner of installing the multi-body intervertebral spinal implant. When the multi-body intervertebral spinal implant comprises a plurality of sections or components the delivery/installation instrument can become complicated. Furthermore, where the number of sections or components of the multi-body intervertebral spinal implant is not determined until the time of installation (i.e. during the spinal surgery), the delivery/installation instrument becomes further complicated.

Accordingly, there presently exists a need for an improved multi-section intervertebral spinal implant delivery/installation device that allows the delivery and construction of a multi-section intervertebral spinal implant in situ.

SUMMARY OF THE INVENTION

The present invention provides instruments for delivering and installing sections of a multi-section intervertebral spinal implant in situ. The multi-section intervertebral spinal implant delivery and installation instruments provide for the sequential deployment and assembling of implant sections into an intervertebral space. An advancement mechanism provides controlled deployment of individual implant sections from the instruments.

Each instrument accepts a plurality of implant sections that are stacked on a deployment rod. Activation of the advancement mechanism advances a pusher thereof against a rearward implant section of the implant section stack. This, in turn, advances all or some of the implant sections such that the forward most implant section exits the instrument. As the advancement mechanism is further activated, additional implant sections are deployed from the instrument. In this manner, a multi-section spinal implant of any number of implant sections may be delivered and assembled in situ (i.e. in an intervertebral space).

In one form, the advancement mechanism comprises an indexing mechanism. The indexing mechanism includes indexers that each have a plurality of teeth or projections situated along their lengths with the teeth being spaced along the indexers so as to define spaces therebetween that correspond in length to the length of an implant section.

In another form, the advancement mechanism comprises a ratchet device provided on and between a trigger and an advancement tube. A pawl or anti-back-out mechanism prevents backward movement thereof.

BRIEF DESCRIPTION OF THE DRAWINGS

The above mentioned and other features, advantages and/or objects of this invention, and the manner of attaining them, will become apparent and the invention itself will be better understood by reference to the following description of embodiments of the invention taken in conjunction with the accompanying drawings, wherein:

FIG. 2 is a side view of the instrument for installing multi-part intervertebral spinal implants of FIG. 1;

FIG. 3 is a front view of the instrument for installing multi-part intervertebral spinal implants of FIG. 1 taken along line 3-3 of FIG. 2;

FIG. 4 is a bottom view of the instrument for installing multi-part intervertebral spinal implants of FIG. 1 taken along line 4-4 of FIG. 2;

FIG. 5 is a sectional view of the instrument for installing multi-part intervertebral spinal implants of FIG. 1 taken along line 5-5 of FIG. 4;

FIG. 15 is a bottom view of the instrument for installing multi-part intervertebral spinal implants of FIG. 12 taken along line 15-15 of FIG. 13; and FIG. 16 is a sectional view of the instrument for installing multi-part intervertebral spinal implants of FIG. 12 taken along line 16-16 of FIG. 15.

Like reference numerals indicate the same or similar parts throughout the several figures.

Figure 1:
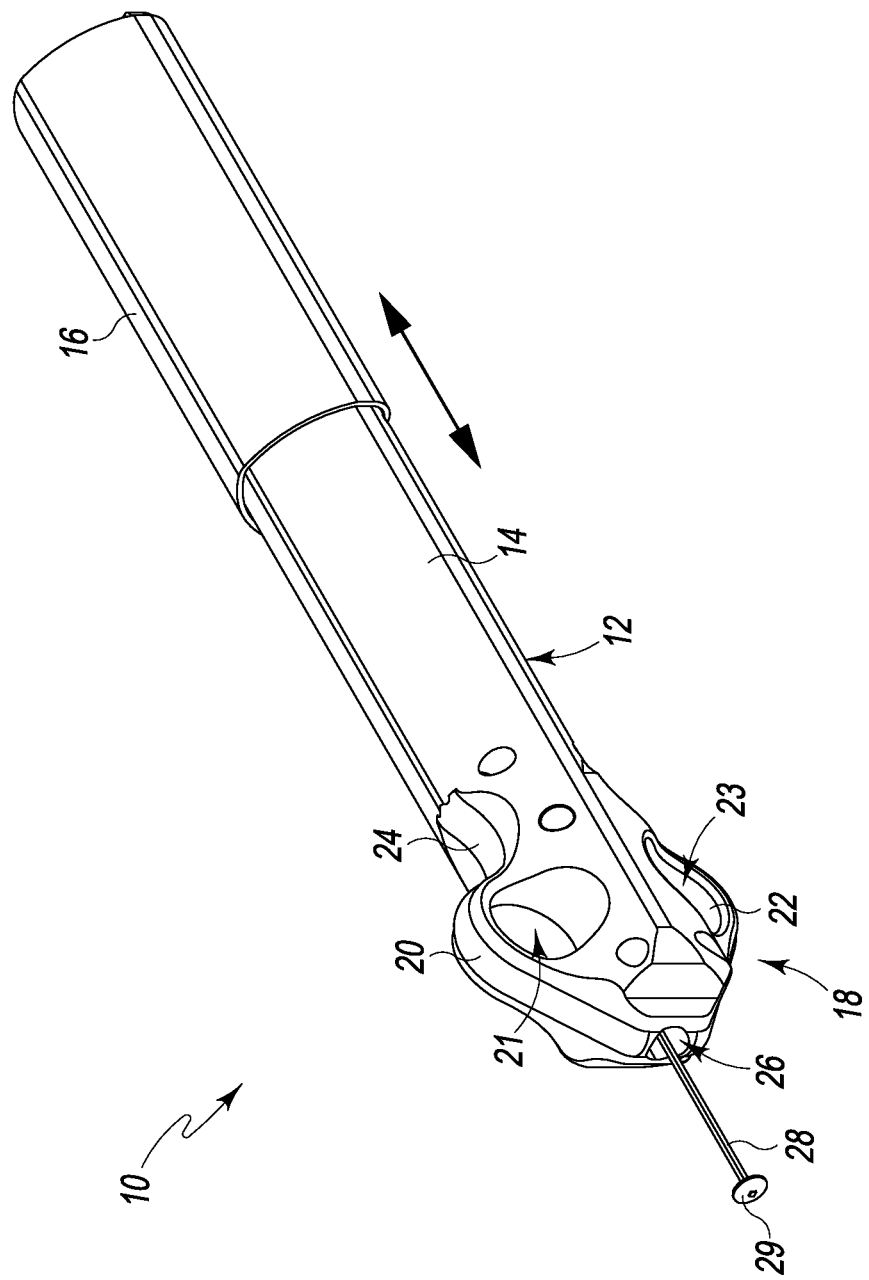
FIG. 1 is a perspective view of a first exemplary embodiment of an instrument for installing multi-part intervertebral spinal implants fashioned in accordance with the principles of the present invention.

A description of the features, functions and/or configuration of the components depicted in the various figures will now be presented. It should be appreciated that not all of the features of the components of the figures are necessarily described. Some of these non-discussed features, if any, as well as discussed features are inherent from the figures. Other non-discussed features may be inherent in component geometry and/or configuration.

DETAILED DESCRIPTION OF EMBODIMENTS OF THE INVENTION

Referring to FIGS. 1-6, there is depicted various views of an instrument for delivering and installing multi-section intervertebral spinal implants, generally designated 10 (the "instrument 10"). The instrument 10 is configured to introduce, situate and assemble a multi-section intervertebral spinal implant, i.e. a spinal implant that is formed of multiple stacked sections, between two adjacent vertebrae. As such, the instrument 10 is configured to hold a plurality of spinal implant sections 30 (see, e.g. FIGS. 5 and 6).

The instrument 10 has a body 12 formed of a main portion 14 and a movable handle 16. The body 12 is generally tubular or cylindrical. The movable handle 16 is likewise generally tubular or cylindrical and overlies an end of the main body portion 14. Axial movement of the shaft 16 is represented by the double-headed arrow. A hand grip 18 is fashioned at an end of the main body portion 14 opposite the movable handle 16. The hand grip 18 is formed by a first loop 20 that defines a first hole 21 and a second loop 22 that defines a second hole 23. The first and second holes 21, 23 are first and second finger holes for allowing fingers of the user to be placed therein in order to hold the instrument 10. A depression 24 is also formed in the main body portion 14 which defines another finger area. In this manner, one hand of the user can hold the instrument 10 by placing a finger in each one of the finger holes 21, 23 and one in the finger depression 24.

Figure 6:
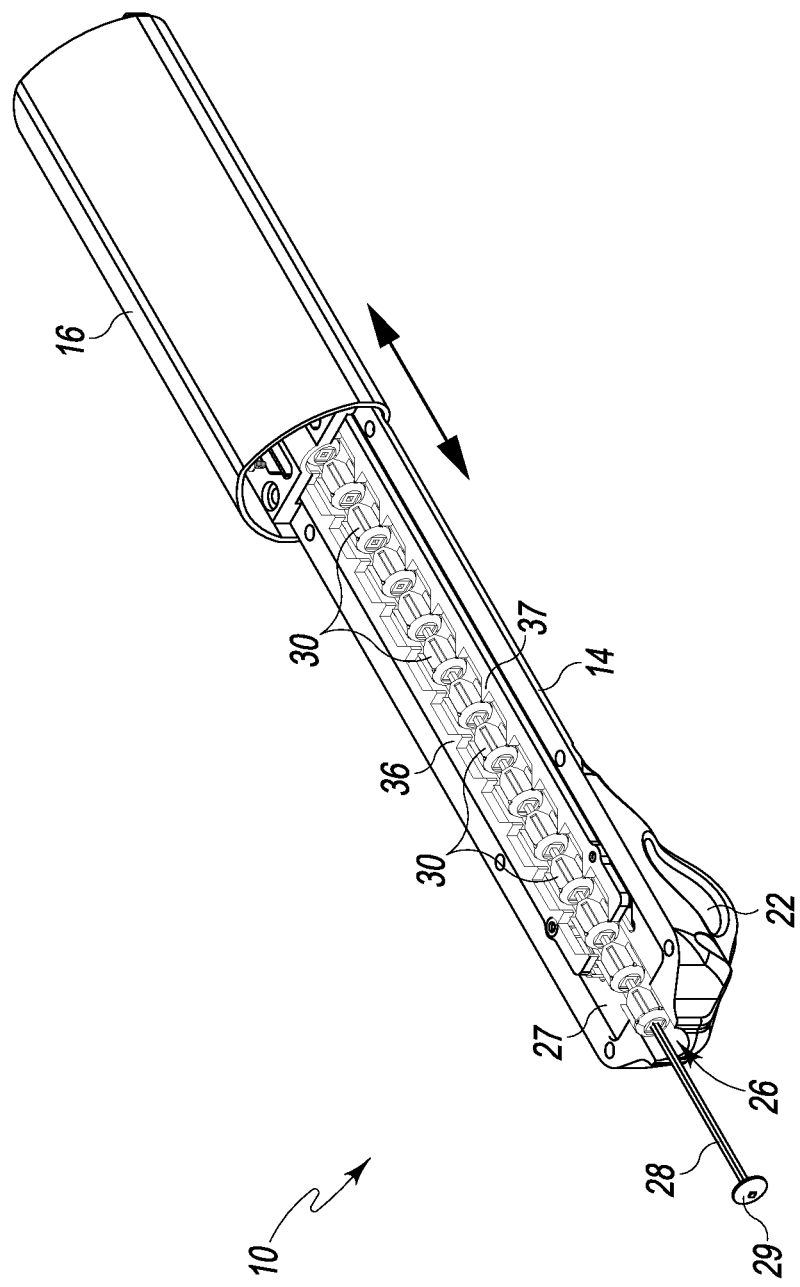
FIG. 6 is a perspective view of the instrument for installing multi-part intervertebral spinal implants of FIG. 1 wherein a portion of the body thereof has been removed to show an indexing mechanism thereof for deploying sections of a multi-part intervertebral spinal implant.
Figure 7:
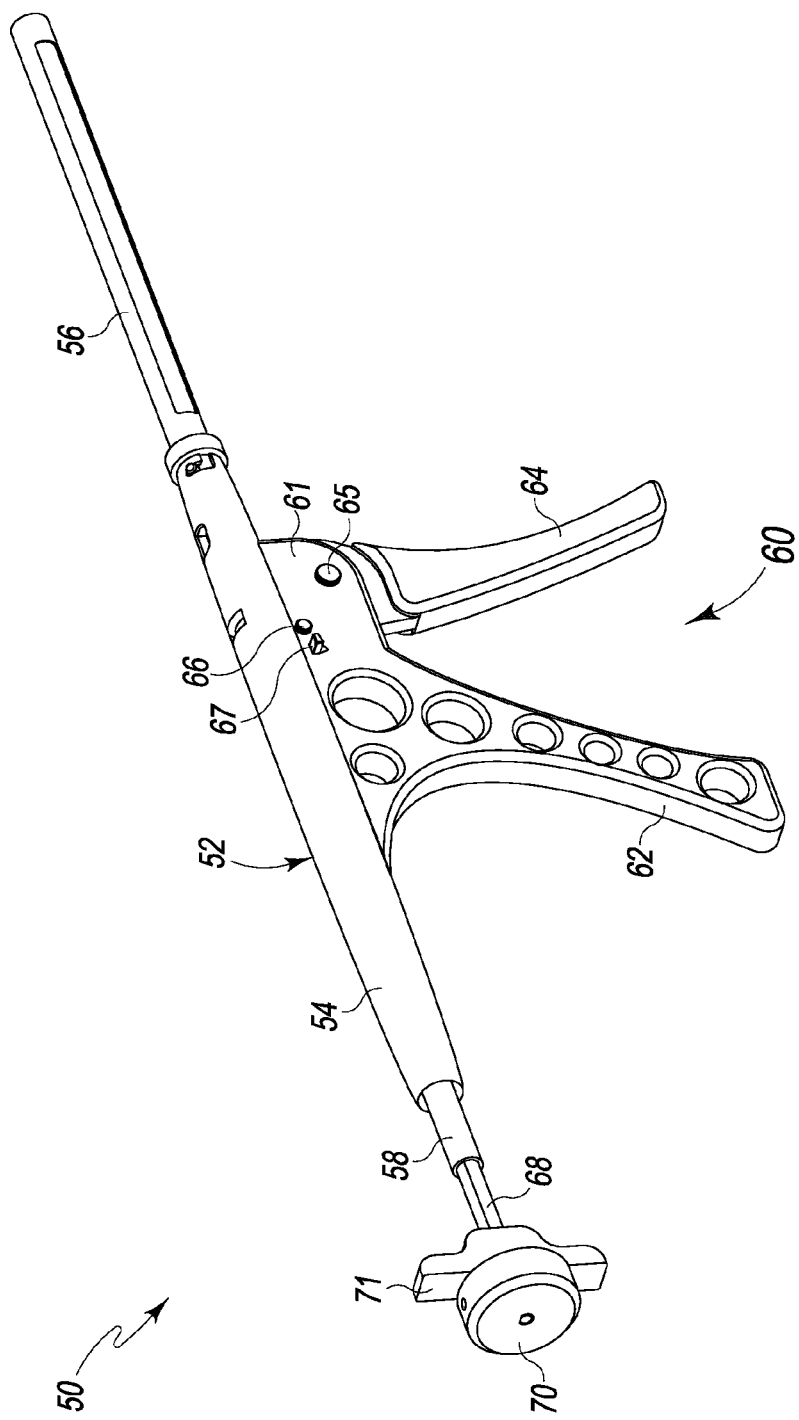
FIG. 7 is a perspective view of a second exemplary embodiment of an instrument for installing multi-section intervertebral spinal implants fashioned in accordance with the principles of the present invention.
Figure 8:
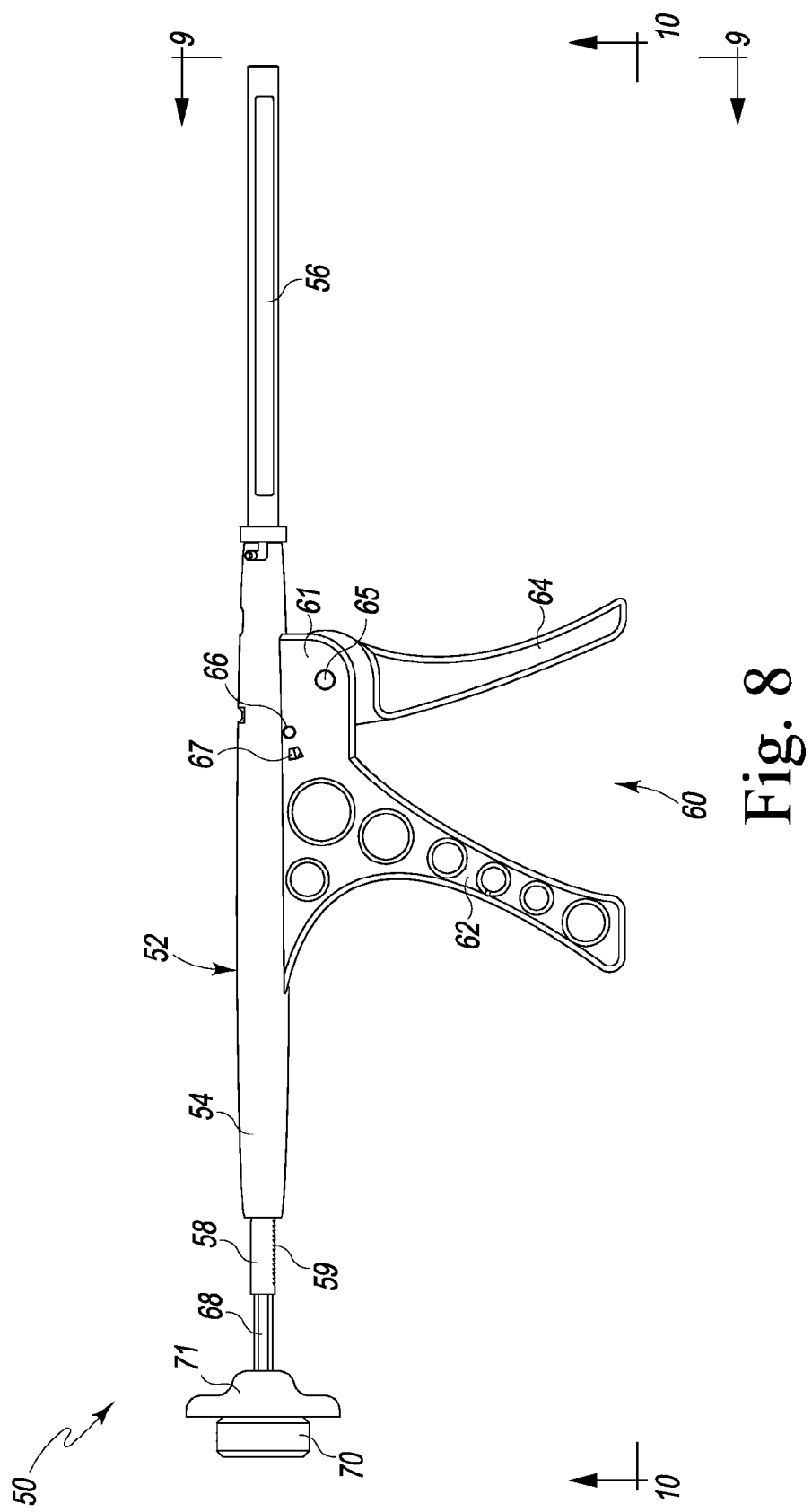
FIG. 8 is side view of the instrument for installing multi-part intervertebral spinal implants of FIG. 7.
Figure 9:
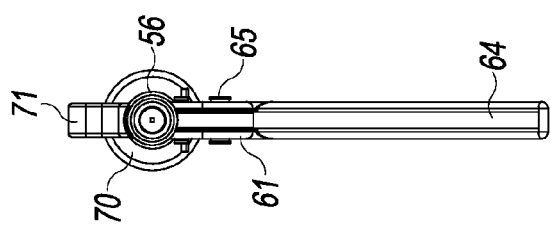
FIG. 9 is a front view of the instrument for installing multi-part intervertebral spinal implants of FIG. 7 taken along line 9-9 of FIG. 8.
Figure 10:
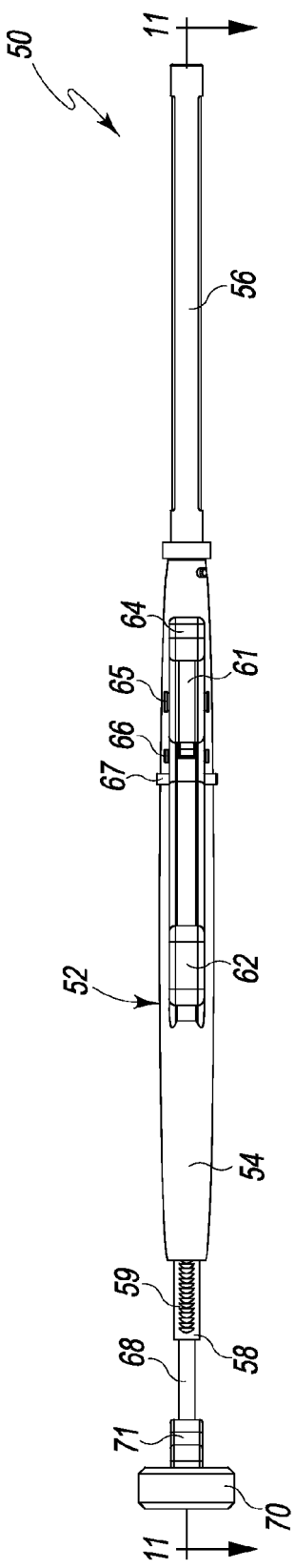
FIG. 10 is a bottom view of the instrument for installing multi-part intervertebral spinal implants of FIG. 7 taken along line 10-10 of FIG. 8.

As best seen in FIGS. 5 and 6, the main body portion 14 has an internal cavity 27 in which is disposed an indexing mechanism formed by first and second indexers 36 and 37. The first and second indexers 36, 37 each have a plurality of teeth or projections situated along their lengths with the teeth being spaced along the indexers so as to define spaces therebetween that correspond in length to the length of an implant section 30. A rod 28, having a plurality of the implant sections 30 situated thereon, is shown disposed in the cavity 27. The rod 28 is sized so as to extend the length of the cavity 27 which is the length of the main body portion 14. The rod 28 also extends beyond the cavity 27 through an opening 26 in the main body portion at the hand grip end. The rod 28 terminates in an end cap 29. The end cap aids in placing the rod 28 with its implant sections 30 into the instrument 10 for deployment therefrom. Also, the main body portion 14 includes a sinuous slot 32. A flexible metal pushing rod 33 (of which only an end portion thereof can be seen) is disposed within the sinuous slot 32. The purpose and function thereof will be described below with respect to the operation of the instrument 10.

Operation of Instrument 10

Before the instrument 10 can be used, a plurality of implant sections 30 must first be placed on the rod 28. After placement of the implant sections 30 on the rod 28, the rod 28 is loaded into the instrument 10. The stationary hand of the user grasps the hand grip 18 (places fingers in the finger holds 21, 23 and 24), while the other hand grasps the movable shaft 16. As the shaft 16 is moved towards the stationary hand (the hand grip 18), the indexing mechanism (indexers 36, 37) engage the implant sections 30 to advance them forward one slot. Also, while the handle 16 is moving towards the hand grip 18, the flexible shaft 33 moves inside the sinuous slot 32. As the flexible shaft 33 is compressed by handle movement, the flexible shaft 33 moves inside the sinuous slot 32 and pushes the leading implant section 30 down the channel 27 to the end of the rod 28. This also deploys a single implant section 30 out of the end opening 26.

After the single implant section 30 has been deployed and the other implant sections 30 have been indexed forward, the handle is moved back to its original position. This makes the flexible shaft 33 retract allowing the indexing mechanism 36, 37 to disengage and move back to their original position. This procedure is repeated until the desired number of implant sections 30 has been deployed. The rod 28 may then be unclamped from the instrument leaving a fully compressed spinal implant.

Referring now to FIGS. 7-11, there is depicted various views of another instrument for delivering and installing multi-section intervertebral spinal implants, generally designated 50 (the "instrument 50"). The instrument 50 is configured to introduce, situate and assemble a multi-section intervertebral spinal implant, i.e. a spinal implant that is formed of multiple stacked sections, between two adjacent vertebrae. As such, the instrument 50 is configured to hold a plurality of spinal implant sections 30 (see, e.g. FIG. 10).

The instrument 50 has a body 52 formed of a main portion 54, a nozzle 56 and a handle/trigger combination 60. The main body portion 54 and the nozzle 56 are generally tubular, with the main body portion 54 defining an internal, longitudinal bore 57 extending therethrough (see FIG. 11) and the nozzle 56 defining an internal, longitudinal bore 72 extending therethrough (see FIG. 11), the internal bore 72 in communication with the internal bore 57. A pusher rod 58 is disposed in the internal longitudinal bore 57, the pusher rod 58 having a row of teeth 59 on an underside thereof. The teeth 59 extend the greater length of the pusher rod 58 and, as described below, allow the pusher rod 58 to be advanced forward by the trigger 64 in order to push out (deploy) the implant sections 30 from an open end 74 of the nozzle 56. A second rod 68 is disposed within the pusher rod 58 and extends the front end of the pusher rod 58 to a rear end of the main body 54. A finger grip 71 is disposed on the rear end of the rod 68 along with a knob 70. A rod holder 73 is disposed at the end of the second rod 58 and is configured to receive an implant section holder rod 76.

The handle/trigger combination 60 is defined by a body 61 that extends from a bottom of the main body 54, a stationary handle 62 and a movable trigger handle 64. The body 61 is shown formed as part of the main body 54. As well, the stationary handle 62 is shown formed as part of the body 61. This does not have to be the case. The movable trigger handle (trigger) 64 is pivotally attached at pivot point 65 to the body 61. The rounded end of the trigger 64 includes a plurality of teeth 75 that are in meshing engagement with the teeth 59 of the pusher rod 58. Pivoting of the trigger 64 by squeezing the trigger towards the stationary handle 62 rotates the rounded end thereby axially moving the pusher rod 58 by the meshing engagement of the teeth 59, 75 (forming a "ratchet"). A pawl 67 is pivotally attached at pivot point 66 to the body 61. The pawl 67 has teeth that mesh with the teeth 59 of the pusher rod 58. When engaged, the pawl 67 prevents backward movement of the pusher rod 58. The pawl 67 may be disengaged to allow backward movement of the pusher rod 58 in order to "reset" the pusher rod 58. This provides an advancement mechanism.

Figure 11:
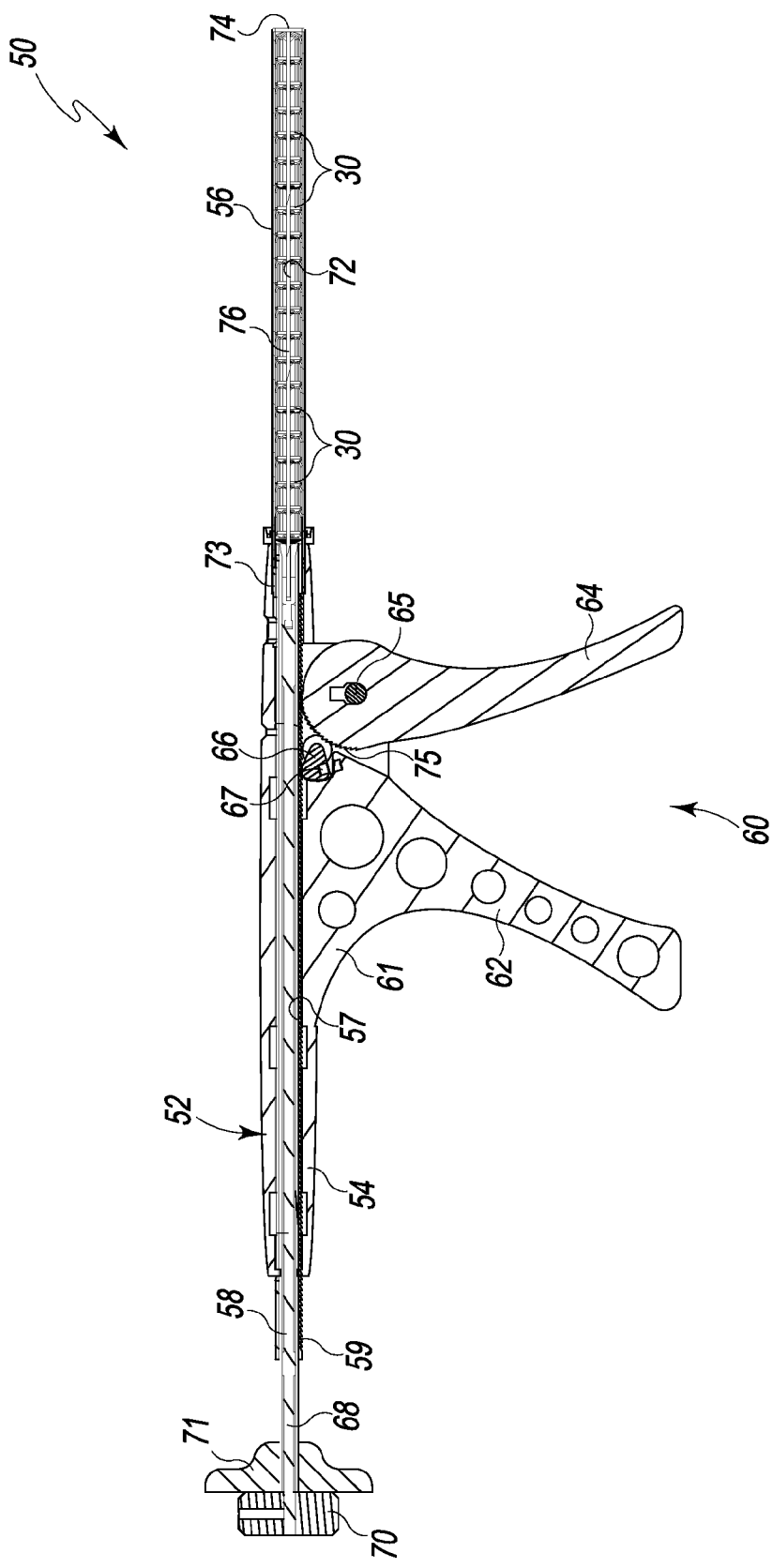
FIG. 11 is a sectional view of the instrument for installing multi-part intervertebral spinal implants of FIG. 7 taken along line 11-11 of FIG. 10.
Figure 12:
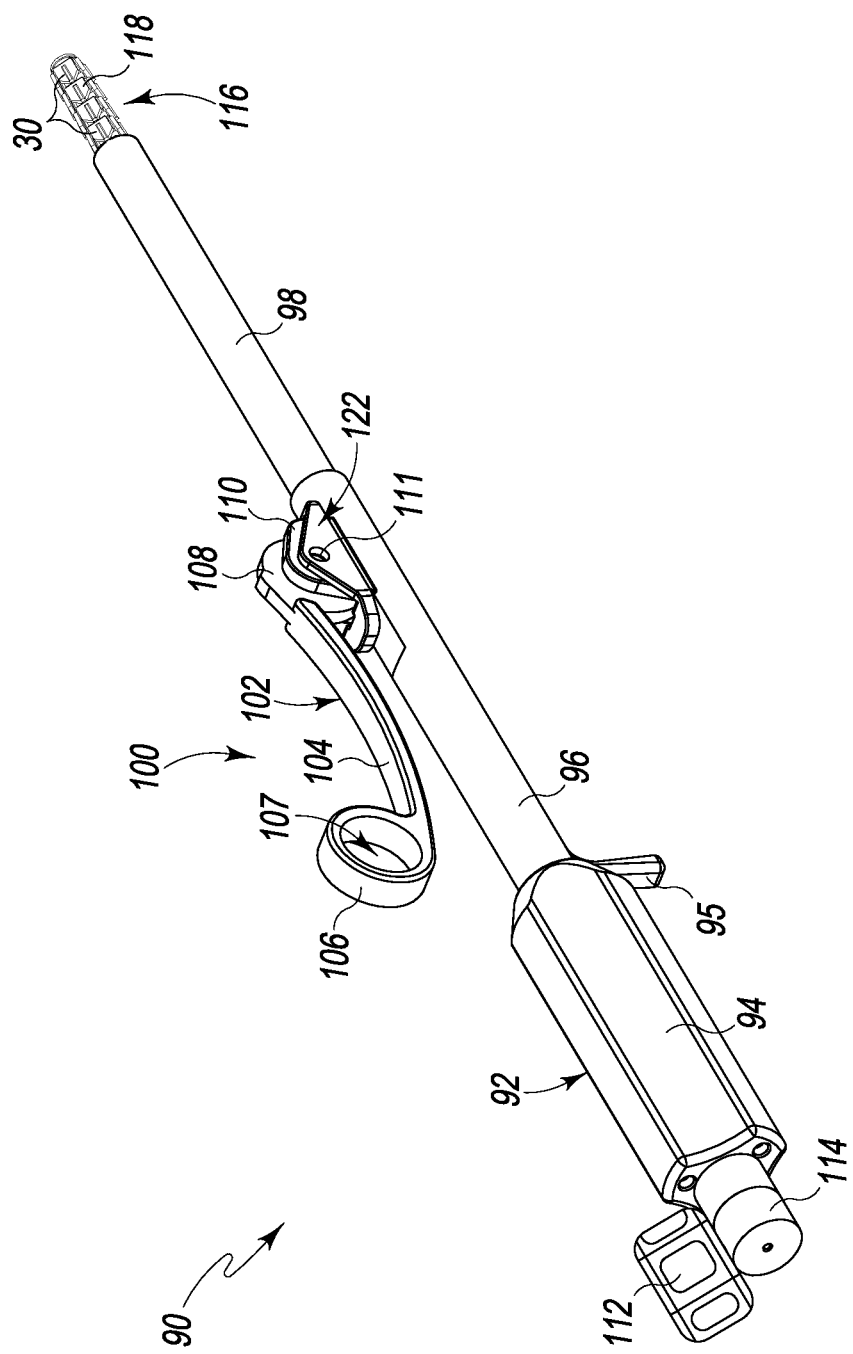
FIG. 12 is a perspective view of a third exemplary embodiment of an instrument for installing multi-section intervertebral spinal implants fashioned in accordance with the principles of the present invention.
Figure 13:
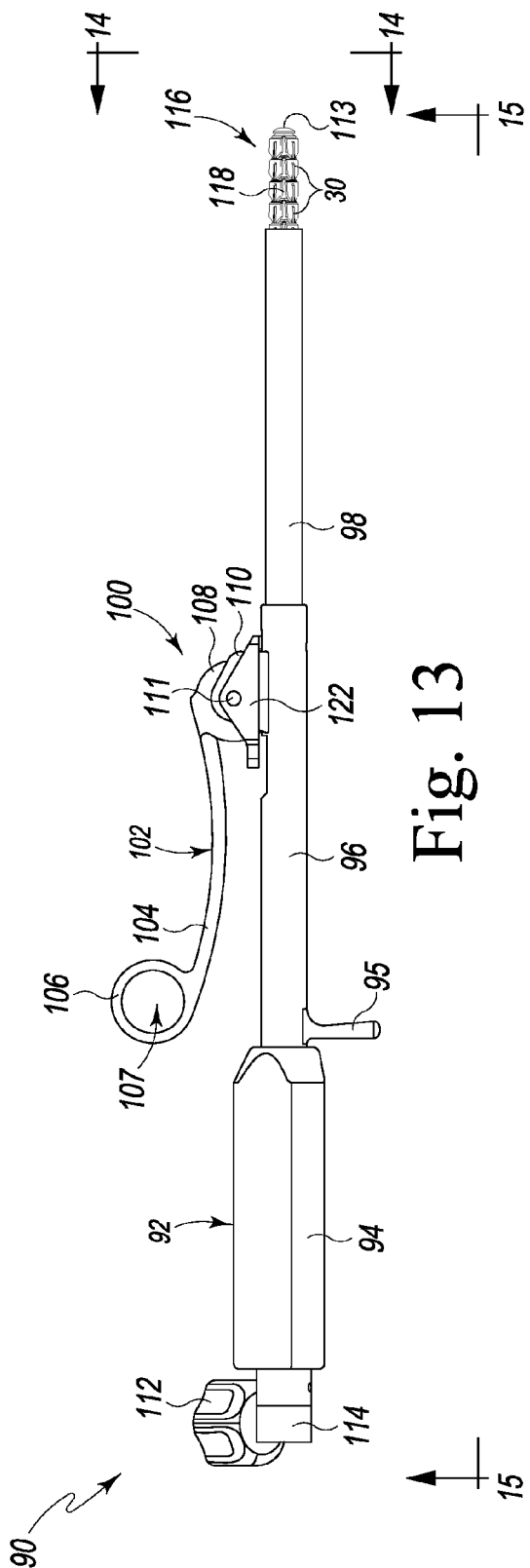
FIG. 13 is side view of the instrument for installing multi-part intervertebral spinal implants of FIG. 12.
Figure 14:
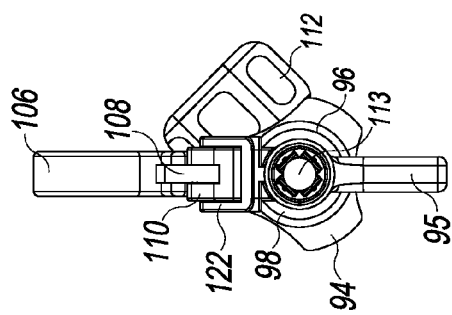
FIG. 14 is a front view of the instrument for installing multi-part intervertebral spinal implants of FIG. 12 taken along line 14-14 of FIG. 13.

As best seen in FIG. 11, the implant section holder rod 76 holds a plurality of implant sections 30 for delivery (deployment) and installation into an intervertebral space. The implant section holder rod 76 with its implant sections 30, is received in the bore 72 of the nozzle 56 through the open end 74 of the nozzle 56. The implant section holder rod 76 is received in the rod holder 73. While the second rod 68 is held stationary, and thus the implant section holder rod 76 is held stationary, axial forward movement of the pusher rod 58 causes the end thereof to push against the implant sections 30 stacked on the implant section holder rod 76 (i.e. advances or pushes against the implant section stack) to deploy an implant section 30 from the end 74 of the nozzle 56. This provides advancement of the implant sections 30. Axial forward movement of the pusher rod 58 is effected by squeezing of the trigger 64.

Operation of Instrument 50

Before the instrument 50 can be used, a plurality of implant sections 30 must first be placed on or stacked onto the rod 76. After placement of the implant sections 30 on the rod 76 into nozzle 56, the assembly is loaded into the instrument 50. The end of the rod 76 is received in the configured end 73 of the second rod 68. Knob 70 is tightened to lock rod 76. The pusher rod 58 is in its rearward most state. One hand of the user grasps the handle 62 and trigger 64. Squeezing of the trigger 64 causes the teeth 75 thereof to push against the teeth 59 of the pusher rod 58 such that the end of the pusher rod 58 engages or pushes against an innermost implant section 30. The innermost implant section 30 pushes against the other implant sections 30 stacked on the rod 76 to advance an implant section 30 out of the nozzle 56. Thereafter, knob 70 is loosened and the instrument assembly is removed leaving a fully compressed spinal implant.

Referring now to FIGS. 12-16, there is depicted various views of another instrument for delivering and installing multi-section intervertebral spinal implants, generally designated 90 (the "instrument 90"). The instrument 90 is configured to introduce, situate and assemble a multi-section intervertebral spinal implant, i.e. a spinal implant that is formed of multiple stacked sections, between two adjacent vertebrae. As such, the instrument 90 is configured to hold a plurality of spinal implant sections 30 (see, e.g. FIG. 16). More particularly, the instrument 90 is configured to hold a stack 116 of implant sections 30.

The instrument 90 has a body 92 formed of a rear portion 94, a middle portion 96, a front portion or nozzle 98 and an advancement/trigger mechanism 100. The middle portion 96 and the nozzle 98 are generally tubular, while the rear portion 94 is generally triangular in cross section. The middle and rear portions 96, 94 define an internal, longitudinal bore 97 extending therethrough (see FIG. 16). The nozzle 98 defines an internal, longitudinal bore 99 extending therethrough (see FIG. 16) with the internal bore 99 in communication with the internal bore 97. A pusher tube 120 is disposed in the internal longitudinal bore 97, the pusher tube 120 having a row of teeth 121 on an upper side thereof. The teeth 121 extend the greater length of the pusher tube 120 and, as described below, allow the pusher tube 120 to be advanced forward by the handle/trigger 104 (and particularly by teeth 109 of a pawl 108 meshing with the teeth 121 of the pusher tube 120; see FIG. 16) in order to push out (deploy) the implant sections 30 from an open end of the nozzle 98. Particularly, the front end 124 of the pusher tube 120 engages an end cap 113 of the stack 116 to push/engage the implant sections 30.

A knob 112 is disposed on an end 114 of the rear portion 94 that is used to secure the rod 118 of the implant stack 116. As seen in FIG. 16, the rod 118 extends through the pusher tube 120 and into the end 114. The knob 112 includes a threaded set pin that extends through a threaded bore in the end 114 such that rotating the knob 112 in one direction tightens the set pin into the rod 118. Rotation of the knob 112 in the opposite direction loosens the set pin from engagement with the rod 118 in order to extract the rod 118.

The handle/trigger/activation mechanism combination 102 is defined by a handle 104 that extends from a bracket 110 on the top of the middle portion 96. The handle 104 is pivotally connected to the bracket 110 via a pivot pin 111. A loop 106 is formed at the end of the trigger 104 and defines a finger hole 106. A projection 95 is provided at the bottom of the middle portion 96 onto which a finger may rest. A rounded end (pawl) 108 of the trigger 64 includes a plurality of teeth 109 that are in meshing engagement with the teeth 121 of the pusher tube 120. Pivoting of the trigger 104 by pulling down of the trigger towards the body 96 rotates the rounded end 108 thereby axially moving the pusher tube 120 by the meshing engagement of the teeth 109, 121 (forming a "ratchet"). A backout prevention mechanism 122 is provided about the bracket 110 that has, among other features, a tooth that engages the teeth 121 of the tube 120 to prevent backward movement of the pusher tube 120. The backout prevention mechanism 122 may be disengaged to allow backward movement of the pusher tube 120 in order to "reset" the pusher tube 120. This provides an advancement mechanism.

As best seen in FIG. 16, the implant section stack 116 holds a plurality of implant sections 30 on the rod 118 for delivery (deployment) and installation into an intervertebral space. The implant section stack 116 with its implant sections 30, is received in the bore 99 of the nozzle 98 through the open end of the nozzle 98. Axial forward movement of the pusher tube 120 causes the end thereof to push against the end cap 113 that is on the rod 118 and rearward of the implant section stack (i.e. advances or pushes against the implant section stack) to deploy an implant section 30 from the end of the nozzle 98. This provides advancement of the implant sections 30. Axial forward movement of the pusher tube 120 is effected by downward movement of the trigger 104.

Operation of Instrument 90

Before the instrument 90 can be used, a plurality of implant sections 30 must first be placed on or stacked onto the rod 118 to form the implant section stack 116. After placement of the implant sections 30 on the rod 118, the implant section stack 116 is loaded into the instrument 90. Particularly, the stack 116 is inserted into the front of the nozzle 98. The end cap 113 holds the implant sections forward since the rod 118 extends all the way through the instrument 90 and into the end 114. The end of the rod 118 is then secured to the end 114 by rotating the knob 112. Compression of the tube 120 is ratcheted forward (advanced) using the handle 104 with the finger in the finger hole 107. As the compression tube 120 advances forward, the end 124 pushes against the end cap 113 which, in turn, pushes against the implant sections 30. As the implant sections 30 exit the nozzle 98 they expand. The backout prevention mechanism 122 prevents the compression tube 120 from moving backwards when the handle 104 is ratcheting back to a home position. The end cap 113 pushes against the fully expanded implant sections thereby creating a fully assembled and locked spinal implant. Thereafter, the rod grip handle is loosened and the instrument assembly is removed leaving a fully compressed spinal implant.

While the invention has been illustrated and described in detail in the drawings and foregoing description, the same is to be considered as illustrative and not restrictive in character, it being understood that only preferred embodiments have been shown and described and that all changes and modifications that come within the spirit of the invention are desired to be protected.

What is claimed is:

1. An instrument for installing a multi-section spinal implant into an intervertebral space one spinal implant section of a plurality of implant sections of the multi-section spinal implant at a time, the instrument comprising:
   a body having a main portion and a moveable portion moveable along the main portion, the main portion comprising a longitudinal bore extending from a rear opening in the main portion to a front opening in the main portion;
   a deployment rod situated in the longitudinal bore and holding a plurality of stacked spinal implant sections; and
   a flexible shaft having a first end connected to the moveable portion and a second end extending into the longitudinal bore and adjacent an end spinal implant section of the plurality of stacked spinal implant sections, wherein movement of the moveable portion moves the flexible shaft to push against the end spinal implant section of the plurality of stacked spinal implant sections to deploy a beginning spinal implant section of the plurality of stacked spinal implant sections from the front opening of the main portion.

2. The instrument of claim 1, wherein the body comprises a slot, and wherein the flexible shaft movably extends through the slot, wherein movement of the moveable portion moves the flexible shaft within the slot.

3. The instrument of claim 1, wherein the deployment rod is removable from the longitudinal bore to place the plurality of spinal implant segments thereon.

4. An instrument for installing a multi-section spinal implant into an intervertebral space one spinal implant section of a plurality of implant sections of the multi-section spinal implant at a time, the instrument comprising:
   a body having a longitudinal bore extending from a rear opening in the body to a front opening in the body;
   a deployment rod situated in the longitudinal bore and holding a plurality of stacked spinal implant sections;
   a sleeve situated about the deployment rod within the longitudinal bore and having an end that is adjacent an end spinal implant section of the stacked plurality of spinal implant sections; and
   a trigger pivotally connected to the body;
   wherein pivotal movement of the trigger advances the sleeve against the end spinal implant section of the stacked plurality of spinal implant sections to deploy a beginning spinal implant section of the plurality of stacked spinal implant sections from the front opening of the body.

5. The instrument of claim 4, wherein the trigger extends laterally from the body and provides pivotal motion upon squeezing the trigger.

6. The instrument of claim 5, wherein the trigger forms part of a handle of the instrument with the handle having a handle portion extending laterally from the body adjacent the trigger.

7. The instrument of claim 4, wherein the trigger extends co-axially from the body and provides pivot motion upon raising and lowering of the trigger.

8. The instrument of claim 7, wherein the trigger forms part of a handle of the instrument with the handle having a handle portion extending laterally from the body on a side of the body opposite the trigger.

9. The instrument of claim 8, wherein the trigger has a finger holder on an end thereof to allow the trigger to be pivoted by a finger of a user.

10. An instrument for introducing a multi-section spinal implant into an intervertebral spinal space of a patient, the instrument comprising:
    an elongated body having a longitudinal bore extending from a rear opening in the elongated body to a front opening in the elongated body;
    a deployment rod removably situated in the longitudinal bore and removably holding a plurality of adjacent spinal implant sections of the multi-section spinal implant; and
    a cover extending about and axially movable about a portion of the elongated body;
    a wire movably extending through the elongated body, the wire having a first end connected to the cover and a second end extending into the longitudinal bore and adjacent an end spinal implant section of the plurality of adjacent spinal implant sections, wherein movement of the cover moves the wire within the elongated body to push against the end spinal implant section of the plurality of adjacent spinal implant sections to deploy a beginning spinal implant section of the plurality of stacked spinal implant sections from the front opening of the elongated body.

11. An instrument for introducing a multi-section spinal implant into an intervertebral spinal space of a patient, the instrument comprising:
    an elongated body having a longitudinal bore extending from a rear opening in the elongated body to a front opening in the elongated body;
    a deployment rod removably situated in the longitudinal bore and removably holding a plurality of adjacent spinal implant sections of the multi-section spinal implant; and
    a sleeve situated about the deployment rod within the longitudinal bore and having an end that is adjacent an end spinal implant section of the adjacent plurality of spinal implant sections, the sleeve having a plurality of longitudinally arranged sleeve teeth on one side thereof; and
    a trigger pivotally connected to the elongated body and having a plurality of trigger teeth;
    wherein pivotal movement of the trigger provides engagement of trigger teeth with sleeve teeth to advance the sleeve against the end spinal implant section of the adjacent plurality of spinal implant sections to deploy a beginning spinal implant section of the plurality of adjacent spinal implant sections from the front opening of the elongated body.

12. The orthopedic instrument of claim 11, wherein the trigger extends laterally from the elongated body and provides pivotal motion upon squeezing the trigger.

13. The orthopedic instrument of claim 12, wherein the trigger forms part of a handle of the instrument with the handle having a handle portion extending laterally from the elongated body adjacent the trigger.

14. The orthopedic instrument of claim 11, wherein the trigger extends co-axially from the elongated body and provides pivot motion upon raising and lowering of the trigger.

15. The orthopedic instrument of claim 14, wherein the trigger forms part of a handle of the instrument with the handle having a handle portion extending laterally from the elongated body on a side of the elongated body opposite the trigger.

16. The orthopedic instrument of claim 15, wherein the trigger has a finger holder on an end thereof to allow the trigger to be pivoted by a finger of a user.

* * * * *